US006916894B2

(12) United States Patent
Cammack et al.

(10) Patent No.: US 6,916,894 B2
(45) Date of Patent: Jul. 12, 2005

(54) POLYDIOXABORINES

(75) Inventors: J. Kevin Cammack, Oceanside, CA (US); Seth R. Marder, Tucson, AZ (US); Bernard Kippelen, Tucson, AZ (US)

(73) Assignees: Nitto Denko Corporation (JP); Arizona Board of Regents on Behalf of The University of Arizona, Tucson, AZ (US)

( * ) Notice: Subject to any disclaimer, the term of this patent is extended or adjusted under 35 U.S.C. 154(b) by 151 days.

(21) Appl. No.: 10/235,182

(22) Filed: Sep. 3, 2002

(65) Prior Publication Data

US 2003/0220500 A1 Nov. 27, 2003

Related U.S. Application Data

(60) Provisional application No. 60/369,076, filed on Mar. 29, 2002.

(51) Int. Cl.[7] .............................................. C08F 130/06

(52) U.S. Cl. .................................................... 526/239

(58) Field of Search ........................................ 526/239

(56) References Cited

U.S. PATENT DOCUMENTS 3,256,310 A  6/1966  Weil

FOREIGN PATENT DOCUMENTS

| EP | 1195834 A | 4/2002 |
|----|-----------|--------|
| GB | 960809 A | 6/1964 |
| GB | 964697 A | 7/1964 |
| GB | 1353905 A | 5/1974 |
| JP | 01135899 A | 5/1989 |
| WO | WO 02 12251 A | 2/2002 |

OTHER PUBLICATIONS

Grundsteins, V. et al.; "Interaction in the system boric acid–2–ethyl–2–methylolpropandiol–1, 3 (ethriol)," Latvijas Psr Zinatnu Akademijas Vestis, Kimijas Serija, No. 3, pp. 261–264, 1975.
Hartmann, H.; "Ein einfacter Weg Zu Neuartigen Borhaltigen Spiroverbindungen," Journal Fur Praktische Chemie, vol. 328, No. 5/6, pp. 755–762, 1986.
Hunter, R. et al.; "Allylation Using Allylborates,"Tetrahedron, Elsevier Science Publishers, Amsterdam, NL, vol. 50, No. 3, pp. 871–888, 1994.
Kamars, A. et al.; "PMR–Study of Interaction Between Boric Acid and Beta–diols in Aqueous Acetone Soultions," Latvijas Psr Zinatnu Akademijas Vestis, Kimijas Serija, No. 6, pp. 700–707, 1986.
Katayama, S. et al.; "Total Synthesis of Fulvic Acid," heterocycles, vol. 23, No. 1, p. 227, 1985.

Kitani, H. et al.; "Synthesis and structural optimization of 7–(3,3–disubstituted–1–pyrro lidinyl)–1–cyclopropyl–6–fluoro–1, 4idhyr o–8–me thoxy–4–oxo–3–quinolinecarboxylic acids as antibacterial agents," Bioorganic & Medicinal Chemistry Letters, Oxford, GB, vol. 7, No. 5, pp. 515–520, Mar. 4, 1997.
Kobayashi, Y. et al.; "Nickel–Catalyzed Coupling Reaction of Sterically Congested Cis Bromades and Lithium Alkenylborates," Tetrahedron, Elsevier Science Publishers, Amsterdam, NL, vol. 54, No. 7, pp. 1053–1062, Feb. 12, 1998.
Lapenko, V.L. et al.; "Vinyl Derivatives of 1, 2–isopropylidene–D–glucose 3, 5–monoborate," Journal of General Chemistry in the USSR, vol. 14, No. 7, pp. 1508–1510, Dec. 12, 1978.
Markin, V.S. et al.; "Polymethine Dyes Derived from Organic Complexes of Boron," Mendeleev Chemistry Journal, vol. 29, No. 4, pp. 121–123, 1984.
Matsubara, H. et al.; "Synthesis of mesomorphic polymers having 1, 3, 2–dioxaborinane rings in the main chain," Molecular Crystals and Liquid Crystals Science and Technology, Section A: Molecular Crystals and Liquid Crystals, vol. 241, 1994, pp. 9–15.
Matteson, D.S., et al.; "Synthesis of Boron–Substitute pyrimidines and Borazaroquinazolines," Journal of Organic Chemistry, vol. 43, No. 5, pp. 950–954, Mar. 3, 1978.
Nakayama, Y. et al.; "Synthesis of 10, 11–dihydroleukotriene B4 Metabolies Via A Nickel–Catalysed Coupling Reaction of Cis–bromides and Trans–alkenyl Borates," Journal of Organic Chemistry, vol. 65, No. 3, pp. 707–715, Feb. 11, 2000.
Philipp, A. et al.; "Synthesis and antiallergic properties of some 4H, 5H–pyrano [3,2–c][1]benzopryan–4–one, 4H, 5H–[1]benzothiopyrano[4,3b]pyran–4–one, and 1,4–dihydro– 5h[1]benzothiopyrano[4,3–b]pyridin–4 –one derivatives," Journal of Medicinal Chemistry, vol. 23, No. 12, pp. 1372–1376, Dec. 1980.
Schlemenz, G.P. et al.; "Trimethoxyphenyl compounds, VIII. Boron Heterocycles in preparative natural products chemistry; synthesis of Baeckeol," Liebigs Annalen Der Chemie, pp. 1514–1519, 1976.
Singh, S.B. et al.; "Discovery, total synthesis, HRV 3C–protease inhibitory activity, and structure–activity relationships of 2–methoxystypandrone and its analogues," Bioorganic & Medicinal Chemistry Letters, vol. 11, No. 24, pp. 3143–3146, Dec. 17, 2001.
Vasilevskaya E.I.; "The Use of Boron Chelate Compounds For Spectral Sensitisation of Titanium Dioxide," Scientific & Applied Photography and Cinematography, vol. 31, No. 5, pp. 763–767, 1990.

(Continued)

*Primary Examiner*—Bernard Dentz
(74) *Attorney, Agent, or Firm*—Knobbe Martens Olson & Bear LLP (57) ABSTRACT

Novel polydioxaborines are prepared by polymerizing novel monomers that contain a dioxaborine group. Polydioxaborines are readily soluble, excellent film formers, and have semiconducting properties useful in various applications.

7 Claims, 1 Drawing Sheet-

OTHER PUBLICATIONS

Vegnere, A. et al.; "Boric Acid Esters of Pentantriol–1, 2, 5 and 2–methyl–2–hydroxymethylpropandiol–1, 3 (methriol)," Latvijas Psr Zinatnu Akademijas Vestis, Kimijas Serija, No. 5, pp. 549–555, 1973.

Wagner, Z.R. et al; "Rigid–Flexible Alternating Block Copolymers That Contain Poly (p–phenylene) Units Of Defined Length As The Rigid Blocks," Macromolecules, vol. 34, No. 17, pp. 5740–5743, Aug. 14, 2001.

Zhao, Z. et al.; "Synthesis of Reactive Condensation Products of Acetylacetone and Their Transformation into Deeply Coloured Methine Dyes," Journal Fur Praktische Chmie, vol. 342, No. 3, pp. 249–255, Mar. 2000.

Bally, et al., "Reaction of Beta–Ketoenols with Diphenylborinic Esters," Tet. Lett., No. 44, pp. 3929–3931, (1965).

Görlitz, et al., "On the Formation and Solvolysis of 4–Aryl–2,2–difluoro–6–methyl–1,3,2–(2H)–dioxaborines," Heteroatom Chemistry, vol. 8, No. 2, pp. 147–155 (1997).

Hartmann, "Ein Einfacher Weg zu Neuartigen Borhaltigen Spiroverbindungen," J. Prakt. Chemie, vol. 328, No. 5, pp 755–762 (1986).

Kammler, et al., "Second–order Optical Non–linearity of New 1,3,2–(2H)–Dioxaborine Dyes," J. Chem. Soc., Faraday Trans., vol. 92, No. 6, pp. 945–947 (1996).

March, J., Advanced Organic Chemisty: Reactions, Mechanisms and Structure, Fourth Edition, Wiley–Interscience, New York, 1992, Chapter 2.

March, J., Advanced Organic Chemistry: Reactions, Mechanisms and Structure, Fourth edition, Wiley–Interscience, New York, 1992, Chapter 9.

Narula, et al., "Preparation and Characterization of Salts Containing Cations of Tricoordinate Boron," Inorg. Chem., vol. 23, pp. 4147–4152 (1984).

Odian, G., Principles of Polymerization, John Wiley, New York, $2^{nd}$ Ed., 1981, pp. 7–10.

Reynolds et al., "The Reactions of 2,2–Difluoro–4–methyl-naptho[1,2–e]–1,3,2–dixoaborin and Its [2,1–e] Isomer with N,N–Dimethylformamide," J. Heterocyclic Chem., vol. 6, pp. 375–377, (1969).

Reynolds, et al., "Synthesis of Chromones," J. Heterocyclic Chem., vol. 16, pp 369–370 (1979).

Reynolds, et al., "Styryl Dyes Derived from Bis Boron Diketonates," J. Heterocyclic Chem., vol. 622 pp. 657–659, (1985).

VanAllan, et al., "The Reactions 2,2–Difluoro–4–methyl-naptho[1,2–e]–1,3,2–dioxabroin and Its [2,1–e] Isomer with Carbonyl Compounds and with Aniline," J. Heterocyclic Chem., vol. 6, pp. 29–35, (1969).

FIGURE 1A. SIDE CHAIN POLYDIOXABORINE

FIGURE 1B. MAIN CHAIN POLYDIOXABORINE

POLYDIOXABORINES

RELATED APPLICATION INFORMATION

This application claims priority to U.S. Provisional Patent Application No. 60/369,076, filed Mar. 29, 2002, which is hereby incorporated by reference in its entirety.

BACKGROUND OF THE INVENTION

1. Field of the Invention

This invention relates generally to polydioxaborines. More particularly, it relates to polymers that comprise a 1,3,2-dioxaborine group in the side chain and/or the main chain, and to methods of making them using the corresponding monomers. Preferred polymers have semiconducting properties and, more preferably, are compatible with modem processing techniques such as precision injection molding, extrusion, spin coating and casting.

2. Description of the Related Art

Dioxaborines contain a core six-membered heterocyclic ring with the general formula $C_3O_2B$. Various dioxaborine-containing compounds have been reported, see, e.g., Reynolds et al., "The Reactions of 2,2-Difluoro-4-methylnaptho [1,2-e]-1,3,2-dioxaborin and Its [2,1-e] Isomer with N,N-Dimethylformamide," J. Heterocyclic Chem., vol. 6, pp. 375–377, (1969); Narula, et al., "Preparation and Characterization of Salts Containing Cations of Tricoordinate Boron," Inorg. Chem., vol. 23, pp. 4147–4152 (1984); Hartmann, "Ein Einfacher Weg zu Neuartigen Borhaltigen Spiroverbindungen," J. Prakt. Chemie, vol. 328, no. 5, pp 755–762 (1986); Görlitz, et al., "On the Formation and Solvolysis of 4-Aryl-2,2-difluoro-6-methyl-1,3,2-(2H)-dioxaborines," Heteroatom Chemistry, vol. 8, no. 2, pp. 147–155 (1997); Reynolds, et al., "Styryl Dyes Derived from Bis Boron Diketonates," J. Heterocyclic Chem., vol. 622 pp. 657–659, (1985); Reynolds, et al., "Synthesis of Chromones," J. Heterocyclic Chem., vol. 16, pp 369–370 (1979); VanAllan, et al., "The Reactions of 2,2-Difluoro-4-methylnaptho[1,2-e]-1,3,2-dioxabroin and Its [2,1-e] Isomer with Carbonyl Compounds and with Aniline," J. Heterocyclic Chem., vol. 6, pp. 29–35, (1969); and Bally, et al., "Reaction of Beta-Ketoenols with Diphenylborinic Esters," Tet. Lett., no. 44, pp. 3929–3931, (1965).

Mixtures of 1,3,2(2H)-dioxaborine dyes and poly(methyl) methacrylate have been reported, see Kammler, et al., "Second-order Optical Non-linearity of New 1,3,2-(2H)-Dioxaborine Dyes," J. Chem. Soc., Faraday Trans., vol. 92, no. 6, pp. 945–947 (1996). However, the dioxaborine group was not attached to the polymer.

SUMMARY OF THE INVENTION

The inventors have discovered polydioxaborines and methods for making them. In a preferred embodiment, the polydioxaborine comprises a dioxaborine group of the formula (I)

(I)

wherein $R_1$, $R_2$ $R_3$, $L_1$ and $L_2$ are each independently selected from the group consisting of hydrogen, linking atom, electron withdrawing group, and electron donating group.

The inventors have also discovered dioxaborine monomers useful for making polydioxaborines. In a preferred embodiment, the dioxaborine monomer comprises a dioxaborine group of the formula (I) and at least one polymerizable group that can be polymerized by a chain polymerization technique selected from the group consisting of radical polymerization, cationic polymerization, and transition metal catalysis. Methods of making these monomers are another preferred embodiment. These monomers are preferably polymerized by a chain polymerization technique to form a polydioxaborine.

In another preferred embodiment, the monomer comprises a dioxaborine group of the formula (I), a first reactive group, and a second reactive group, wherein the first reactive group and the second reactive group are each independently selected from the group consisting of epoxy, ester, phenol, acid chloride, carbamoyl chloride, sulfonyl chloride, hydrazide, acid anhydride, isothiocyanate, and isocyanate. These monomers are preferably polymerized by a step polymerization technique to form a polydioxaborine. Methods of making these monomers are another preferred embodiment.

These and other embodiments are described in greater detail below.

DETAILED DESCRIPTION OF THE PREFERRED EMBODIMENTS

Figure 1A:
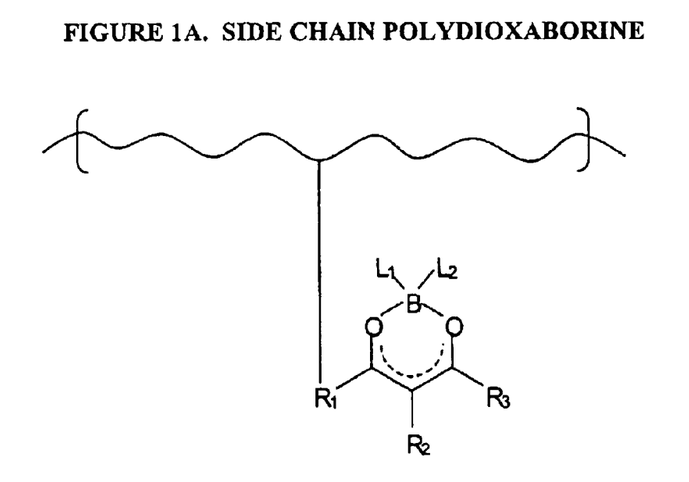
FIG. 1A is a schematic illustration of a side chain polydioxaborine.
Figure 1B:
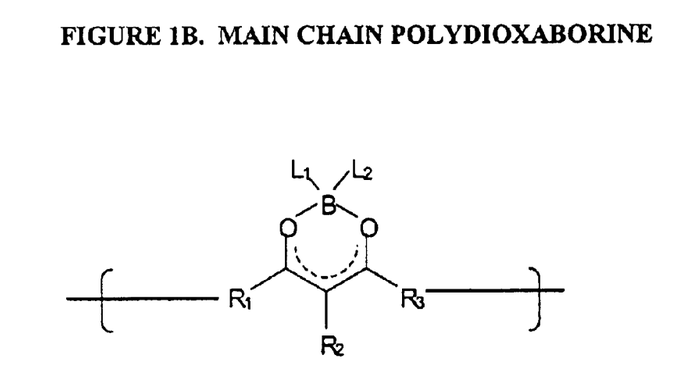
FIG. 1B is a schematic illustration of a main chain polydioxaborine.

A polydioxaborine is a polymer that contains, as part of its structure, at least one core $C_3O_2B$ dioxaborine group. The $C_3O_2B$ dioxaborine groups in the polymer can be attached directly to one another, and/or the polymer can contain other chemical groups in addition to the core $C_3O_2B$ dioxaborine group. For example, in a preferred embodiment, the core $C_3O_2B$ dioxaborine group contains one or more substituents $L_1$, $L_2$, $R_1$, $R_2$ and $R_3$ as shown in structure (I). In structure (I), it will be understood by those skilled in the art that the dashed line indicates a delocalization of charge and the actual structure is the sum of the various resonance structures. To incorporate the core $C_3O_2B$ dioxaborine group into the polymer, it is preferred that one or more of the substituents $L_1$, $L_2$, $R_1$, $R_2$ and $R_3$ is a linking atom or linking group through which the core $C_3O_2B$ dioxaborine group is attached to the rest of the polymer. For example, the core $C_3O_2B$ dioxaborine group can be incorporated into the main chain and/or the side chain of the polydioxaborine polymer by further attachment of the $L_1$, $L_2$, $R_1$, $R_2$ and/or $R_3$ substituents to one another or other groups, as shown schematically in FIG. 1.

Substituents $L_1$, $L_2$, $R_1$, $R_2$ and $R_3$ in formula (I) may represent a variety of chemical groups. Preferably, $L_1$ and $L_2$ are each independently selected from the group consisting of hydrogen, linking atom, electron withdrawing group, and electron donating group. Specific examples of groups that $L_1$ and $L_2$ can each independently represent include hydrogen, linking atom, halogen (e.g., F, Cl, Br, etc.), $C_1$–$C_6$ alkyl, $C_1$–$C_6$ alkoxy, $C_6$–$C_{10}$ aryl, $C_6$–$C_{10}$ aryloxy, $C_1$–$C_6$ thioalkyl, nitrile, $C_1$–$C_6$ acyloxy (e.g., acetyloxy, propionyloxy, etc.), amino, $C_1$–$C_6$ alkylamino, $C_2$–$C_{12}$ dialkylamino, and sulfoxide.

$L_1$ and $L_2$ can together represent a bridging ligand. Non-limiting examples of preferred bridging ligands include the following:

where $Q_{1-10}$ each independently represents a heteroatom, preferably oxygen, capable of forming a covalent or electrostatic bond to boron; where $E_1$ is preferably selected from: $(CR_{a1}R_{a2})_n$, $CR_{a1}=CR_{a2}$, $C\equiv C$, O, S, N—$R_{a3}$ and N=N; where $E_2$ is preferably selected from: $(CR_{a1}R_{a2})_n$, $CR_{a1=CRa2}$, O, S, N—$R_{a3}$ and N=N; where m and n are each independently integers in the range of 1 to 10; and where $R_{a1}$, $R_{a2}$, $R_{a3}$, $R_{a4}$, are preferably each independently H or a linear or branched alkyl group with up to 18 carbons.

Preferably, $R_1$, $R_2$ and $R_3$ are each independently selected from the group consisting of hydrogen, linking atom, electron withdrawing group, and electron donating group. Examples of $R_1$, $R_2$, and $R_3$ include hydrogen, linking atom, carboxylate, carboxylic acid, aldehyde, amide, epoxy, acid chloride, anhydride, nitrile, sulfonate, sulfonic acid, phosphonate, nitrate, nitro, $C_1$–$C_{18}$ alkoxy, $C_1$–$C_{18}$ alkyl, $C_1$–$C_{18}$ fluoroalkyl, hydroxyl, $C_{12}$–$C_{20}$ diarylamino, $C_2$–$C_{10}$ dialkylamino, $C_1$–$C_6$ alkylhalide, $C_1$–$C_6$ nitroalkyl, $C_1$–$C_6$ alkanoic acid, $C_1$–$C_6$ alkylamide, $C_6$–$C_{10}$ aryl, $C_6$–$C_{10}$ aryloxy, $C_7$–$C_{20}$ alkylaryl, and $C_7$–$C_{20}$ alkylaryloxy.

When the core $C_3O_2B$ dioxaborine group is positively charged, an anion is typically associated with the group to achieve overall electroneutrality of the resulting complex. Examples of suitable anions include F$^-$, Cl$^-$, Br$^-$, I$^-$, $CH_3COO^-$, $CF_3SO_3^-$, $NO_3^-$, $BF_4^-$, $PF_6^-$, $SbF_6^-$, $SbCl_4^-$, and $B(C_6H_5)_4^-$.

The core $C_3O_2B$ dioxaborine group may be incorporated into the structure of the polydioxaborine by polymerizing or copolymerizing monomers that contain the core $C_3O_2B$ dioxaborine group. Various preferred ways of making dioxaborine monomers and polymers are discussed below.

Definitions

A "monomer" is molecule containing one or more polymerizable groups. "Comonomers" are monomers having different chemical structures that are polymerized together to form a polymer. A "dioxaborine monomer" is a molecule that contains at least one polymerizable group and at least one core $C_3O_2B$ dioxaborine group.

A "polymerizable group" is a chemical group that reacts with other chemical groups to link monomers together to form a polymer, by either chain or step polymerization mechanisms. Examples of polymerizable groups include acrylate, methacrylate, acrylamide, alkene, alkyne, styrene, cyclic N-phenyliminocarbonate, cyclic acid anhydride, sultam, lactam, lactone, and epoxy. In the monomer context, a "reactive group" is a polymerizable group that participates in a step polymerization by reacting with other functional groups. Examples of reactive groups include epoxy, ester, phenol, acid chloride, carbamoyl chloride, sulfonyl chloride, hydrazide, acid anhydride, isothiocyanate, isocyanate, arylbromide, aryltrialkyltin, arylcuprate, arylzinc, alkyne, alkynecuprate, diarylamine and alkene.

A "polymer" is a large molecule that contains recurring units formed by polymerizing monomers. A polymer may be a "homopolymer" comprising recurring units formed by, e.g., polymerizing a particular monomer, or it may be a "copolymer" comprising recurring units formed by, e.g., copolymerizing two or more different monomers. A polymer has a weight average molecular weight of about 1,000 or greater. A "polydioxaborine" is a polymer that contains, as part of its structure, at least one core $C_3O_2B$ dioxaborine group.

A "chain polymerization technique" is a method for making a polymer that proceeds by a chain polymerization mechanism. A "step polymeriation technique" is a method for making a polymer that proceeds by a step polymerization mechanism. A more detailed description of these terms is found in G. Odian, Principles of Polymerization, John Wiley, New York, $2^{nd}$ Ed., 1981, pp. 7–10. Chain polymerization techniques are often referred to by the type of initiation employed. Examples of chain polymerization techniques include radical polymerization, anionic polymerization, cationic polymerization, and transition metal catalysis (including ring-opening metathesis polymerization).

An "electron donating group" or "donor" is a chemical group that delocalizes electron density towards the group to which it is attached. An "electron withdrawing group" or "acceptor" is a chemical group that attracts electron density from the group to which it is attached. In this context, a hydrogen substituent is neither electron donating nor electron withdrawing. A more detailed description of these terms is found in J. March, Advanced Organic Chemistry: Reactions, Mechanisms and Structure, Fourth Edition, Wiley-Interscience, New York, 1992, Chapter 9, which is incorporated herein by reference.

A "ligand" is a chemical group that can be covalently or electrostatically bound to the boron atom. A "bridge" it is relatively non-reactive molecular fragment that connects two or more chemical groups. A "π-conjugated bridge" is a bridge containing π-bonds that allow delocalization of electrons along the bridge. A "bridging ligand" is a structure having two or more ligands that are connected by a bridge and which complex to the same boron center. The term "bridging ligand" may be used synonymously with the term "chelating ligand" herein.

An "aromatic group" is a cyclic group of carbon atoms that contains 4n+2 π electrons where n is an integer. A "heteroaromatic group" is a cyclic group of atoms, with at least one atom within the ring being an element other than carbon, that contains 4n+2 π electrons where n is an integer. A more complete description of aromaticity and heteroaromaticity can be found in J. March, *Advanced Organic Chemistry: Reactions, Mechanisms and Structure*, Fourth edition, Wiley-Interscience, New York, 1992, Chapter 2, which is incorporated herein by reference. A "heteroatom" is an atom in group IV, V, VI, or VII in the periodic table other than carbon, such as Nitrogen, Oxygen, Silicon, Phosphorous or Sulfur.

A "chromophore" is a molecule or aggregate of molecules that can absorb electromagnetic radiation. An "excited state" is an electronic state of a molecule in which the electrons populate an energy state that is higher than another energy state for the molecule.

A "linking atom" is an atom that is capable of bonding to more than one other atom. Examples of linking atoms are carbon, silicon, nitrogen, phosphorous, oxygen and sulfur. A "linking group" is a group that contains a linking atom. Examples of linking groups that contain a carbon linking atom are —$CH_2$—, —CH=, and —C≡, as well as the —CH= groups in aromatic rings, e.g., —$C_6H_4$—O— and —$C_6H_4$—. Examples of linking groups that contain a nitrogen linking atom are —N= and —NH—. Examples of linking groups that contain a sulfur linking atom are —S— and —$SO_2$—. Examples of linking groups that contain an oxygen linking atom are —O—, —O—$C_6H_4$—, and —O—$SO_2$—O—. The terms "linking atom" or "linking group" are used herein to refer to an atom or group, respectively, through which the core $C_3O_2B$ dioxaborine group is attached to other groups, e.g., the rest of the polydioxaborine or monomer in which the core $C_3O_2B$ dioxaborine group is contained. An asterisk (*) in a chemical structure identifies the atom of attachment to a functional group and indicates that the structure is missing a hydrogen that would normally be implied by the structure in the absence of the asterisk.

Dioxaborine Monomers

A dioxaborine monomer is a molecule that contains at least one polymerizable group and at least one core $C_3O_2B$ dioxaborine group. Preferred dioxaborine monomers contain a dioxaborine of the formula (I) in which a least one of $L_1$, $L_2$, $R_1$, $R_2$ and $R_3$ is a polymerizable group, or a linking atom through which the dioxaborine of the formula (I) is attached to the polymerizable group. Preferred methods for making dioxaborine monomers are discussed below.

A preferred dioxaborine monomer synthesis method proceeds by first forming the dioxaborine group as illustrated in Scheme (IIa) below for $L_1=L_2=F$:

The reactants in Scheme (IIa) can be purchased from commercial sources or readily synthesized by methods known to those skilled in the art. The reaction is preferably conducted by combining the reactants in an excess of acid anhydride at a temperature in the range of 40–80° C. for a period of time in the range of about 2–24 hours. Following cooling, the product is preferably isolated by filtration of the precipitated product from the reaction mixture or, in the case of materials soluble in the acid anhydride, by removal of the acid anhydride, optionally washing the residue with water, and chromatographic separation. Preferably, chromatographic separation is achieved by elution of the product from silica or alumina with an organic solvent or mixture of organic solvents such as ethyl acetate, hexane, methylene chloride and/or toluene.

Another preferred dioxaborine monomer synthesis method proceeds by first forming the dioxaborine group as illustrated in Scheme (IIb) below for $L_1=L_2=F$, alkoxy, OH, CN, fluoroalkyl, alkyl, aryl, thiolate, sulfonyl, etc. $BL_3S$ represents the complex $BL_3$ which may optionally be a neutral solvent adduct of $BL_3$, for example $BF_3(OEt_2)$ (when L=F); the neutral compound $BL_3$; or an ionic complex $BL_3X$ where X=H, CN, alkoxy, L, etc.:

The reactants in Scheme (IIb) can be purchased from commercial sources or readily synthesized by methods known to those skilled in the art. In a preferred method, the diketone is dissolved in an organic solvent such as dichloromethane or acetic acid, preferably of low polarity (7>ϵ>2) (where ϵ is the relative permittivity at 20° C.). Preferably, the solvent forms an azeotrope with the protonated form of L or has a higher boiling point than L. An approximately equimolar quantity of $BL_3$ is then added to the reaction mixture. The reaction vessel is fitted with a condensor and the reaction mixture is heated. The HL formed on condensation of the diketone and the $BL_3$ is distilled out of the reaction mixture until the reaction is complete. After cooling, the product is preferably isolated by filtration of the precipitated product from the reaction mixture or, in the case of products soluble in the reaction solvent, by optionally washing thereaction mixture with water, followed by chromatographic separation. Preferably, chromatographic separation is achieved by elution of the product from silica or alumina with an organic solvent or mixture of thereof such as ethyl acetate, hexane, methylene chloride and/or toluene.

Another preferred dioxaborine monomer synthesis method proceeds by first forming the dioxaborine group as illustrated in Scheme (IIc) below in which $L_1=L_2=Cl$, Br, CN, fluoroalkyl, etc., R is alkyl and $BL_3S$ represents the complex $BL_3$ which optionally may be a neutral solvent adduct of $BL_3$, or preferably the neutral compound $BL_3$.

The reactants in Scheme (IIc) can be purchased from commercial sources or readily synthesized by methods known to those skilled in the art such as those described in

Scheme IIb. In a preferred method, the dialkylborondiketonate is dissolved in a organic solvent such as chloroform, preferably aprotic and of relatively low polarity (7>ε). Preferably, the product is not soluble in the reaction solvent. The solution of dialkylborondiketonate is added to a solution containing between one and 10 equivalents of $BL_3$ maintained at a constant temperature between −78 and 35° C. The reaction mixture is allowed to stir for 3–24 hours at which time the precipitated product can be isolated by filtration. Alternately, during the course of the reaction, a less polar solvent such as pentane or carbon tetrachloride may be added to precipitate the product. The product may then be further purified by crystallization from a suitable organic solvent or mixture.

Another preferred dioxaborine monomer synthesis proceeds by first forming the dioxaborine group as illustrated in Scheme (IId) below for bridging ligand $L_1,L_2$=bridging diol, bridging diacid, bridging bis(diarylamine), bridging bis(dialkylamine), etc.:

The reactants in Scheme (IId) can be purchased from commercial sources or readily synthesized by methods known to those skilled in the art. In a preferred method, the diketone is dissolved in an organic solvent such as toluene or dichloroethane which preferably forms an azeotrope with water. An approximately equimolar quantity of bridging ligand and boric acid is added to the reaction mixture. The reaction vessel is fitted with a condensor and the reaction mixture is heated to reflux. The water byproduct is removed from the reaction mixture by azeotropic distillation or is directly distilled out of the reaction mixture for 3–48 hours. The precipitated product can be isolated by filtration or, in the case of products soluble in the reaction solvent, by optionally precipitating the reaction mixture with water, followed by crystallization. The product may then be further purified by recrystallization from a suitable organic solvent or mixture of solvents.

Preferably, at least one of $L_1$, $L_2$, $R_1$, $R_2$ and/or $R_3$ in the product of Scheme (II) contains or is modified to contain a functional group that facilitates subsequent attachment to a polymerizable group. Preferably, $R_1$ contains or is modified to contain a hydroxyl, thiol, acid, acid chloride, or aldehyde group that facilitates attachment to a polymerizable group by forming an ester, ether or amide bond. For example, Scheme (III) below illustrates the reaction of acryloyl chloride with the product of Scheme (II) to form a dioxaborine monomer in which the dioxaborine group is attached to a polymerizable acrylate group:

The reaction between acryloyl chloride and the product of Scheme (II) is preferably performed under dry conditions in an aprotic solvent. Those skilled in the art will understand that the dioxaborine monomer that is the product of Scheme (III) contains a dioxaborine of the formula (I) in which the carbon in the phenyl ring to which the dioxaborine ring is attached is a linking carbon atom.

Another preferred dioxaborine monomer synthesis method proceeds by the direct condensation of the dioxaborine monomer, as illustrated in Scheme (IVa) below in which $L_1=L_2=F$ and at least one of $R_1$, $R_2$ $R_3$ is a linking atom or polymerizable group as defined above:

The product illustrated in Scheme IVa can be synthesized by the method outlined for Scheme IIa.

Another preferred dioxaborine monomer synthesis proceeds as illustrated in Scheme (IVb) in which bridging ligand $L_1,L_2$=bridging diol, bridging diacid, bridging bis(diarylamine), bridging bis(dialkylamine), etc., and at least one of L, $R_1$, $R_2$ $R_3$ is a polymerizable group as defined above:

The product illustrated in Scheme IVb can be synthesized by the method outlined for Scheme IId above.

Polydioxaborines

Polydioxaborines can be prepared in various ways. In a preferred embodiment, polydioxaborines are prepared by using a chain polymerization technique to polymerize a dioxaborine monomer. In another preferred embodiment, polydioxaborines are prepared by using a step polymerization technique to polymerize a dioxaborine monomer. Both of these embodiments are described in greater detail below. Those skilled in the art will understand that the identity of the substituents on the core $C_3O_2B$ dioxaborine group, e.g., $L_1$, $L_2$, $R_1$, $R_2$ and $R_3$ in formula (I), and the nature of the linkage between the core $C_3O_2B$ dioxaborine group and the polymerizable group is provided in the description of the dioxaborine monomers above. For ease of illustration, various dioxaborine monomers discussed below are represented by a polymerizable group attached to a box labeled "DB". In these illustrations, DB represents a chemical group that comprises the core $C_3O_2B$ dioxaborine group, and preferably represents a group of the formula (I). Details regarding the nature of DB and its linkage to the polymerizable group or the resulting polymer may be understood by reference to the descriptions of the corresponding monomers above.

In a preferred embodiment, polymerization is accomplished by using a chain polymerization technique, more preferably a chain polymerization technique selected from the group consisting of radical polymerization, cationic polymerization, and transition metal catalysis. Acrylates, methacrylates and acrylamides are preferably polymerized by radical polymerization as shown schematically in Scheme (V):

Styrenes may be polymerized by cationic polymerization or transition metal catalysis, preferably by radical polymerization, as shown in Scheme (VI):

Alkynes are preferably polymerized by transition metal catalysis or radical polymerization, and alkenes are preferably polymerized by transition metal catalysis, as illustrated in Scheme (VII):

Transition metal catalysis can also proceed by a ring opening metathesis polymerization mechanism (ROMP), as illustrated in Scheme (VIII) for a dioxaborine monomer having an cyclopentenyl polymerizable group. For polymerization by ROMP, the dioxaborine monomer preferably comprises a cyclic polymerizable group containing an alkene, more preferably a carbocyclic alkene selected from the group consisting of norbornadienyl, cyclopropenyl, cyclobutenyl, cyclopentenyl, and norbornenyl.

Cyclic N-phenyliminocarbonate, cyclic acid anhydride, sultam, lactam, lactone, and cyclic ether polymerizable groups are preferably polymerized by cationic polymerization that proceeds by ring-opening of the polymerizable group. For example, Scheme (IX) illustrates the cationic ring-opening polymerization of a dioxaborine monomer having an epoxy polymerizable group:

Free radical polymerization may be conducted in various solvents or in the bulk state and is preferably performed by intermixing a free radical initiator with the monomers. The amount of free radical initiator is preferably in the range of about 0.001% to about 1%, by weight based on monomer weight, depending on the efficiency of the initiator and the molecular weight desired for the resulting polymer. Various free radical sources known in the art may be used, including thermal initiators that contain an O—O, S—S, N—O or N=N bond, e.g., acyl peroxides such as acetyl peroxide and benzoyl peroxide, as well as azo compounds such as azobisisobutyronitrile (AIBN); and redox initiators that comprise a reductant and an oxidant, e.g., peroxides in combination with reducing agent such as ferrous ion, and combinations of inorganic reductants and oxidants, e.g., combinations of reductants such as $HSO_3^-$, $SO_3^{2-}$, $S_2O_3^{2-}$, and $S_2O_5^{2-}$ with oxidants such as $Ag^+$, $Cu^{2+}$, $Fe^{3+}$, $ClO_3^-$, and $H_2O_2$. If a solvent is used, it is preferred that the solvent have a low chain transfer constant if high molecular weight polymers are desired, preferably a chain transfer constant lower than the chain transfer constant of the monomer. If the polymer molecular weight is higher than desired, chain transfer agents may be added as needed to control molecular weight. Preferred chain transfer agents include triethylamine, di-n-butyl sulfide, and di-n-butyl disulfide.

Cationic polymerization may be conducted in various solvents and is preferably performed by intermixing an acid with the monomers. The amount of acid is preferably in the range of about 0.001% to about 1%, by weight based on monomer weight, depending on the molecular weight desired for the resulting polymer. Suitable acids include protonic acids and Lewis acids. Protonic acids preferably comprise an anion that is not highly nucleophilic, to reduce termination of the growing polymer chain by combination. Preferred protonic acids include perchloric, sulfuric, phosphoric, fluoro- and chlorosulfonic, methanesulfonic and trifluoromethanesulfonic. Lewis acids are preferred for obtaining high molecular weight polymers. Preferred Lewis acids include metal halides (e.g., $AlCl_3$, $BF_3$, $SnCl_4$, $SbCl_5$, $ZnCl_2$, $TiCl_4$, and $PCl_5$), organometallic derivatives (e.g., $RAlCl_2$, $R_2AlCl$, $R_3Al$, where R is $C_1$–$C_5$ alkyl), and oxyhalides ($POCl_3$, $CrO_2Cl$, $SOCl_2$, and $VOCl_3$). Polymerization using Lewis acids is preferably conducted in a polar aprotic solvent such as tetrahydrofuran that contains a small amount of a proton donor such as water or an alcohol, or more preferably a small amount of a cation donor such as t-butyl chloride.

Polymerization by transition metal catalysis is preferably conducted by intermixing the monomers with a transition metal catalyst. The amount of transition metal catalyst is preferably in the range of about 0.001% to about 1%, by weight based on monomer weight. Preferred transition metal catalysts comprise a Group I–III organometallic compound (or hydride) and a compound of a Group IV–VIII transition metal. Examples of suitable Group I–III organometallic compounds include $R_nAlCl_{3-n}$, $R_2Be$, $R_2Mg$, RLi, $R_4AlLi$, RNa, $R_2Cd$, $R_3Ga$ and phenylmagnesium bromide, where n is 1, 2 or 3 and R is $C_1$–$C_5$ alkyl. Examples of Group IV–VIII transition metal compounds include $TiCl_4$, $TiCl_3$, $TiBr_3$, $VCl_4$, $VCl_3$, $R_2TiCl_2$, $Ti(OR)_4$, $Ti(OH)_4$, $MoCl_5$, NiO, $CrCl_3$, $ZrCl_4$, $WCl_6$, and $MnCl_2$, where R is $C_1$–$C_5$ alkyl. Since many of these compounds are water sensitive, polymerizations are preferably conducted in dry aprotic solvents such as alkanes, tetrahydrofuran, dioxane, etc.

Copolymerizations can be conducted using chain polymerization techniques and various mixtures of monomers. Preferably, a dioxaborine monomer is intermixed with a comonomer and polymerized as described above to form a copolymer. The comonomers can be intermixed prior to polymerization, or added over the course of the polymerization, individually or in combination. Suitable comonomers include the dioxaborine monomers described herein, as well as other monomers. Preferably, copolymerizations are conducted using comonomers having mutually compatible polymerizable groups, so that a desirable distribution of comonomer recurring units in the resulting copolymer is obtained. Monomers copolymerizable with the dioxaborine monomers described herein thus include $C_1$–$C_{18}$ alkyl acrylates, $C_1$–$C_{18}$ alkyl methacrylates, $C_2$–$C_6$ hydroxyalkyl acrylates, $C_2$–$C_6$ hydroxyalkyl methacrylates, styrene, $C_1$–$C_5$ substituted styrenes, acrylamide, $C_1$–$C_4$ substituted acrylamides, acetylene, ethylene, vinyl halide, tetrafluoroethylene, vinyl acetate, butadiene, $C_1$–$C_{18}$ alkyl-substituted 1-alkenes, $C_1$–$C_{18}$ alkoxy-substituted 1-alkenes, $C_7$–$C_{14}$ cyclic N-phenyliminocarbonate, $C_1$–$C_{10}$ cyclic acid anhydride, $C_1$–$C_{10}$ sultam, $C_1$–$C_{10}$ lactam, $C_1$–$C_{10}$ lactone, and $C_1$–$C_{10}$ cyclic ether (e.g., epoxy).

Amounts of comonomers used are preferably in the range of nil to about 99.9%, more preferably about 0.01% to about 25%, by weight based on total weight of monomers, to produce copolymers having the corresponding levels of recurring units. More preferably, the comonomer content (if any) is adjusted to control the properties of the resulting polymer, e.g., to adjust solubility, glass transition temperature (Tg), melting point, and/or semiconducting properties. For example, copolymerization of a dioxaborine monomer with 2-ethylhexylacrylate has been found to produce a copolymer having a Tg that is lower than the homopolymer formed by polymerization of the dioxaborine monomer alone. Excessive amounts of 2-ethylhexylacrylate, however, tend to adversely affect the semiconducting properties of the polymer.

In another preferred embodiment, polydioxaborines are prepared by a step polymerization technique. Step polymerizations are preferably conducted using dioxaborine monomers that contain two reactive groups, although small amounts of monomers containing lesser or greater numbers of reactive groups, e.g., one or three, may also be present. The reactive groups are selected so that they react with one another in high yield to form a chemical bond or group that links the monomers together to form a polymer. For example, hydroxyl groups react with carboxylic acids, acid halides, or alkyl esters to form ester linkages, and with sulfonyl halides to form sulfonic acid esters. The two different reactive groups can be present on the same monomer or on different monomers. For example, polydioxaborines that contain ester linkages can be made using a dioxaborine monomer that contains an acid chloride reactive group and a hydroxyl reactive group as shown in Scheme (X):

(X)

Polydioxaborines that contain ester linkages can also be made using two different dioxaborine monomers, one containing the hydroxyl groups and the other containing the carboxylic acid, acid chloride, or alkyl ester groups, e.g., as shown in Scheme (XI).

For ease of illustration, the polymerization of dioxaborine monomers to form polydioxaborines may be illustrated below by reference to one of these methods, e.g., by using a dioxaborine monomer that contains both types of reactive groups as in Scheme (X). Those skilled in the art will understand that the description below of either method applies to both methods, unless otherwise stated, e.g., that the reactive groups can also be on different monomers as shown in Scheme (XI). In many cases, a monomer that contains two different reactive groups is preferred because its use leads to a balanced stoichiometry and higher molecular weights. However, such a monomer may be more difficult to prepare or obtain, and thus the use of monomers that differ from each other may be preferred in some cases. Those skilled in the art further understand that, when two different monomers are used, e.g., as shown in Scheme (XI), higher molecular weights are generally obtained by balancing the stoichiometry so that the amounts of each reactive group are about equal, except where noted below.

Preferred polydioxaborines contain linkages between dioxaborine groups that are formed by high yield reactions between the reactive groups of the dioxaborine monomers discussed above. Preferred linkages include ester, amide, urethane, siloxane, amine, and carbonate. Ester linkages are preferably formed by reaction between monomers comprising the following pairs of reactive groups: hydroxyl and carboxylic acid, hydroxyl and alkyl ester, preferably methyl ester, and hydroxyl and acid halide. The hydroxyl group is preferably a phenol (attached to an aromatic group). Polydioxaborines that contain ester linkages can also be formed by the reaction of a diol with an acid anhydride, where the diol and/or the acid anhydride comprise a dioxaborine group. The reaction between hydroxyl and acid halide is preferred because the other reactions involve the elimination of water, typically under basic conditions that may adversely affect the dioxaborine. The reaction tends to be faster when the hydroxyl group is attached to an aromatic group. The reaction between hydroxyl and acid halide, preferably acid chloride, is preferably conducted at room temperature or below in a dry polar aprotic solvent. The presence of a non-nucleophilic acid acceptor, such as a trialkylamine, in the reaction mixture may be helpful to capture the acid eliminated during the polymerization, e.g. HCl. The polydioxaborine can be isolated from the resulting solution by adding the solution to an excess of non-solvent, followed by filtration and rinsing. Copolymers can be made by using mixtures of dioxaborine monomers, and/or by intermixing the dioxaborine monomer(s) with other monomers containing the appropriate reactive groups as discussed above. Examples of preferred comonomers include $C_1$–$C_{18}$ diols, $C_1$–$C_{18}$ diacid halides, $C_1$–$C_{18}$ diacids, and $C_1$–$C_{18}$ dialkyl esters.

Amide linkages are preferably formed by reaction between monomers comprising the following pairs of reactive groups: amine and carboxylic acid, and amine and acid halide. Polydioxaborines that contain amide linkages can also be formed by the reaction of a diamine with an acid anhydride, where the diamine and/or the acid anhydride comprise a dioxaborine group. The reaction between amine and acid halide is preferred because the amine is a base that may adversely affect the dioxaborine at high temperatures. The reaction between amine and acid halide, preferably acid chloride, is preferably conducted at room temperature or below in a dry polar aprotic solvent. When a diacid halide monomer and a diamine are used, the polymerization may be conducted under interfacial polymerization conditions in which the diacid halide monomer is dissolved in an organic solvent, the diamine is dissolved in water, and the resulting organic solvent and aqueous solution are stirred together to facilitate polymerization at the interface between the two phases. The presence of a non-nucleophilic acid acceptor, such as a trialkylamine, in the reaction mixture is helpful to capture the acid eliminated during the polymerization, e.g. HCl, and to prevent the acid from protonating the amine and reducing its reactivity. In the case of solution polymerization, the polymer may be isolated by adding the polymer solution to a non-solvent, filtering, rinsing and drying. In the case of interfacial polymerization, the polymer is preferably withdrawn from the stirred mixture over the course of the polymerization. Sulfonamide linkages can also be formed similarly, by reaction between a sulfonyl halide reactive group and an amine. Copolymers can be made by using mixtures of dioxaborine monomers, and/or by intermixing the dioxaborine monomer(s) with other monomers containing the appropriate reactive groups as discussed above. Examples of preferred comonomers include $C_1$–$C_{18}$ diamines, $C_1$–$C_{18}$ diacid halides, $C_1$–$C_{18}$ sulfonyl halides, and $C_1$–$C_{18}$ acid anhydride.

Urethane linkages are preferably formed by reaction between monomers comprising the following pairs of reactive groups: hydroxyl and diisocyanate, or hydroxyl and carbamoyl halide. The hydroxyl group is preferably a phenol (attached to an aromatic group). Urethanes are preferably formed by reacting a monomer containing two hydroxyl groups (a diol) with a monomer containing two isocyanate groups (a diisocyanate), where either or both of the monomers comprises a dioxaborine group. Isocyanates tend to undergo side reactions, so a slight excess of isocyanate groups over hydroxyl groups is preferred. Polymerization is preferably conducted by mixing the monomers together in a dry polar aprotic solvent, more preferably at room temperature or below. The presence of about 0.1% to about 1.0 of a tertiary amine or organometallic catalyst is often helpful. Dibutyltin dilaurate is a preferred catalyst. Copolymers can be made by using mixtures of dioxaborine monomers, and/or by intermixing the dioxaborine monomer(s) with other monomers containing the appropriate reactive groups as discussed above. Examples of preferred comonomers include $C_1$–$C_{18}$ diols, $C_1$–$C_{18}$ diisocyanates, and $C_1$–$C_{18}$ carbamoyl halides.

Dioxaborine polymers that contain siloxane linkages may be prepared from monomers that contain siloxane linkages and terminal functional groups. For example, dioxaborine monomers that contain siloxane polymerizable groups can be polymerized where the polymerizable groups contain reactive groups such as alkene and silane, as shown in Scheme (XII) below:

(XII)

The reaction between alkene and silane groups shown in Scheme (XII) is catalyzed by chloroplatinic acid. Siloxane polymerizable groups bearing other pairs of reactive groups can also be employed, e.g., hydroxyl and acetoxy; amine and epoxy, etc. Polymerization may be conducted in an organic solvent such as toluene or tetrahydrofuran, or in the bulk, optionally in the presence of a catalyst. Siloxanes have low glass transition temperatures, good chemical resistance, good transparency, and good thermal properties, and these polydioxaborines are preferred in a number of applications. Copolymers can be made by using mixtures of dioxaborine monomers, and/or by intermixing the dioxaborine monomer(s) with other monomers containing the appropriate reactive groups as discussed above. Examples of preferred comonomers include $Si_3$–$Si_{50}$ dihydroxy siloxanes, $Si_3$–$Si_{50}$ diamino siloxanes, $Si_3$–$Si_{50}$ diacetoxy siloxanes, $Si_3$–$Si_{50}$ diepoxy siloxanes, and $Si_3$–$Si_{50}$ divinyl siloxanes.

Amine linkages are preferably formed by reacting a diepoxy monomer and a diamine monomer, where either or both of the monomers comprises a dioxaborine group, as illustrated in Scheme (XIIII). When a primary diamine monomer is used, the resulting secondary amine linkage in the polymer can undergo further reaction with other epoxy groups, leading to crosslinking. Thus, the ratio of the two monomers is not necessarily 1:1, and is preferably adjusted to control the degree of crosslinking in the resulting polymer. The monomers are preferably intermixed and reacted together in bulk. The amine reactive groups are less active when bonded to an aromatic group, and thus aliphatic diamines are preferred for ambient and low temperature polymerizations. Copolymers can be made by using mixtures of dioxaborine monomers, and/or by intermixing the dioxaborine monomer(s) with other monomers containing the appropriate reactive groups as discussed above. Examples of preferred comonomers include $C_1$–$C_{18}$ diepoxides, preferably bisphenol A, and $C_1$–$C_{18}$ diamines.

(XIII)

Carbonate linkages may be formed by reacting phosgene with a diol, preferably a diphenol, where the diol contains a dioxaborine group as illustrated in Scheme (XIV). Preferably, the diol and phosgene are intermixed in an organic solvent that contains a non-nucleophilic base, preferably a trialkylamine, to neutralize the by-product hydrogen halide, at a temperature in the range of about 0° C. to about 50° C. Carbonate linkages may also be formed by reacting a dibenzyl halide, preferably a dibenzyl bromide, with potassium carbonate, where the dibenzyl halide contains a dioxaborine group. Preferably, the dibenzyl halide and potassium carbonate are intermixed in a polar aprotic solvent in the presence of a crown ether.

(XIV)

Hydrazide linkages are preferably formed by reacting a hydrazide with an acid halide. Preferably, a dihydrazide monomer and a diacid chloride monomer are polymerized, where either or both of the monomers comprises a dioxaborine group as illustrated in Scheme (XV). The dioxaborine groups can be the same or different. The polymerization is preferably conducted at room temperature or below in a dry polar aprotic solvent. The presence of a non-nucleophilic acid acceptor, such as a trialkylamine, in the reaction mixture may be helpful to capture the acid eliminated during the polymerization, e.g. HCl. The polydioxaborine can be isolated from the resulting solution by adding the solution to an excess of non-solvent, followed by filtration and rinsing. Copolymers can be made by using mixtures of dioxaborine monomers, and/or by intermixing the dioxaborine monomer(s) with other monomers containing the appropriate reactive groups as discussed above. Examples of preferred comonomers include $C_1$–$C_{18}$ dihydrazides and $C_1$–$C_{18}$ diacid halides.

(XV)

Polydioxaborines that contain hydrazide linkages can be reacted further with amines to form polydioxaborines that contain triazole groups. This reaction is preferably performed in the presence of a strong acid, more preferably polyphosphoric acid, at a temperature in the range of about 100° C. to about 200° C., preferably about 150° C. to about 190° C., for periods of time ranging from about 2 hours to about 1 week. Preferably, polydioxaborines that contain hydrazide linkages are reacted with aniline to form polydioxaborines that contain phenyl-substituted triazole groups.

The weight average molecular weights of the polydioxaborines are preferably about 1,000 or greater, more preferably about 5,000 or greater, most preferably in the range of about 10,000 to about 10,000,000. Molecular weights are preferably measured by high pressure size exclusion chromatography, using polystyrene standards. In the absence of crosslinking, higher molecular weights are usually easier to achieve by chain polymerization than by step polymerization. Those skilled in the art will understand that many polymerizable groups, e.g., epoxy, may be polymerized by either step or chain polymerization techniques. Preferred polydioxaborines are stable to air and acid, soluble in a variety of polar organic solvents such as acetone and acetonitrile, and have excellent film forming properties.

EXAMPLES

The following examples are provided for the purposes of further describing the preferred embodiments, and do not limit the scope of the invention described herein.

Example 1

A round bottom flask was charged with 4-hydroxyacetophenone (20 g, 0.147 mol), acetic anhydride (100 mL, 1.06 mol) and a stir bar. The reaction mixture was stirred at 120° C. overnight to give a solution of the acetate ester. The mixture was then cooled to room temperature. In a separate flask, an acetic acid (50 mL) solution of boron trifluoride bis acetic acid complex (27.8 mL, 0.300 mol) was heated to 60° C. The solution of acetophenone-4-acetate was added to the $BF_3$/acetic acid solution over the course of an hour. The reaction mixture was allowed to stir overnight at 60° C., and then cooled to room temperature. Isolation of a small amount of the yellow crystalline solid showed it to be the acetate ester of the dioxaborine intermediate. $^1$H NMR (400 MHz, Acetone-$d_6$) δ: 8.24 (d, J=9 Hz, 2H), 7.40 (d, J=9 Hz, 2H), 7.08 (s, 1H), 2.46 (s, 3H), 2.31 (s, 3H) ppm. $^{13}$C NMR (100 MHz, Acetone-$d_6$) δ: 194.3, 181.3, 168.3, 157.0, 130.7, 128.7, 122.9, 97.8, 23.9, 20.2 ppm. The solution was carefully quenched with aqueous sodium acetate (68.0 g, 0.5 mol in 200 mL $H_2O$), at which time the reaction mixture turned black and a tarry mass separated. The quenched mixture was heated at reflux for 2H, and then poured into ice water (500 mL). The product was extracted with ethyl acetate and then chromatographed on silica (ethyl acetate/hexanes 3:7 v/v). Removal of the solvent in vacuo gave the product as microcrystalline yellow solid (23.82 g, 91%). $^1$H NMR (400 MHz, Acetone-$d_6$) δ: 7.8 (d, 2H, J=8.8 Hz), 7.7 (d, 2H, J=8.8 Hz), 6.1 (s, 1H), 4.1 (s, 3H), 2.3 (s, 3H) ppm.

Example 2

A 3-necked flask was charged with the title compound in example 1 [1-(4-hydroxyphenyl)-1,3-butanedione] (2.00 g, 11.22 mmol), acrylic acid (0.77 mL, 11.22 mmol), ethyl acetate and a stir bar. The flask was fitted with a drying tube, and the solution was stirred at room temperature. Dicyclohexylcarbodiimide (DCC) (2.54 g, 12.3 mmol) and catalytic 4-dimethylamino-pyridine (DMAP) (12 mg, 0.11 mmol) were added to the reaction mixture. The reaction mixture was allowed to stir at room temperature in the dark overnight. The resulting slurry was filtered, the supernatant collected and the solvent removed in vacuo. The residue was adsorbed on silica and eluted from a silica gel column with ethyl acetate/hexanes (1:5 v/v). Removal of the solvents in vacuo yielded the product as a white crystalline solid (1.08 g, 41%). $^1$H NMR (400 MHz, $CDCl_3$) δ: 7.91 (d, J=8.8 Hz, 2H), 7.24 (d, J=8.8 Hz, 2H), 6.64 (d, J=17.6 Hz, 1H), 6.33 (m, 1H), 6.15 (s, 1H), 6.05 (1H, J=10.3 Hz, 1H), 2.20 (s, 3H).

Example 3

A 3-necked flask was charged with $BF_3$ acetic acid complex (15.51 mL, 111.5 mmol), acetic acid (50 mL) and a stir bar and fitted with a drying tube. The stirring solution was heated in air to 60° C. A solution of 1-(4-hydroxyphenyl)-1,3-butanedione (9.93 g, 55.73 mmol) in acetic acid (50 mL) was added dropwise to the reaction mixture over the course of 2 hours. The reaction mixture was allowed to stir at 60° C. overnight, then cooled to room temperature. Isolation of the resulting yellow precipitate by filtration, followed by crystallization from $CHCl_3$ gave the hydroxy substituted dioxaborine complex as bright yellow needles (7.5 g, 60.0%). $^1$H NMR (400 MHz, $CDCl_3$) δ: 8.00 (d, J=8.8 Hz, 2H), 6.95 (d, J=8.8 Hz, 2H), 6.44 (s, 1H), 6.16 (br s, 1H), 2.35 (s, 1H) ppm.

Example 4

A round bottom flask containing 4-hydroxy acetophenone (30.00 g, 220 mmol), acryloyl chloride (228 mmol, 18.1 mL), calcium oxide (36.80 g, 660 mmol) and toluene (mL) was fitted with a condenser and a drying tube. A stir bar was added to the reaction mixture and the stirred slurry was heated to 60° C. for 19 hours. The reaction mixture was cooled to room temperature and filtered. The supernatant was washed 3 times with 50 mL saturated aqueous NaHCO$_3$ and dried over Na$_2$SO$_4$. Removal of the solvent in vacuo followed by crystallization from CH$_2$Cl$_2$/hexanes gave the product as a white crystalline solid (18.0 g, 42%). $^1$H NMR (400 MHz, CDCl$_3$) δ: 8.0 (d, 2H, J=8.7 Hz) 7.2 (d, 2H, J=8.7 Hz), 6.6 (d, 1H, J=17 Hz), 6.3 (m, 1H) 6.0 (d, 1H, J=9.5 Hz), 2.6 (s, 3H).

Example 5

A 3-necked flask was charged with the title compound in example 3 (4.35 g, 19.2 mmol), 4-dimethylaminopyridine (20 mg), THF (60 mL) and triethylamine (6.16 mL, 50.0 mmol). The flask was fitted with a drying tube, placed in an ice/water bath and allowed to cool for 1H. Neat acryloyl chloride (2.03 mL, 25.00 mL) was added to the cooled mixture dropwise over 5 minutes. The mixture was stirred at 0° C. for one hour, then allowed to warm to room temperature for one hour. Following a standard aqueous workup, the solvent was removed in vacuo. The residue was adsorbed on silica and the product eluted with ethyl acetate/hexanes (3:7 v/v). Removal of the solvent gave the product as straw-yellow crystals (2.69 g, 50%). $^1$H NMR (400 MHz, CDCl$_3$) δ: 8.10 (d, J=8.8 Hz, 2H), 7.34 (d, J=8.8 Hz, 2H), 6.62 (d, J=17.6 Hz, 1H), 6.54 (s, 1H), 6.33 (dd, J$_1$=17.6 Hz, J$_2$=10.3 Hz, 1H), 6.09 (d, J=10.3 Hz, 1H), 2.41 (s, 3H) ppm. $^{13}$C (100 MHz, CDCl$_3$) δ: 192.8, 181.8, 163.5, 156.3, 133.9, 130.7, 128.7, 127.3, 122.5, 97.4, 24.9 ppm.

Example 6

A solution of BF$_3$ diethyl etherate (3.25 mL, 26.0 mmol) in hexanoic anhydride was heated to 50° C. The title compound from example 4 (2.47 g, 13.0 mmol) was added to the stirring solution as a neat solid in 100 mg aliquots over a 2 hour period. The mixture was allowed to continue stirring at 50° C. for 16H. On cooling to room temperature, CH$_2$Cl$_2$ (100 mL) was added to the reaction mixture and the resulting solution was then washed with saturated aqueous NaHCO$_3$ (100 mL). The organic layer was collected. Elution from silica in CH$_2$Cl$_2$/hexanes (1:1 v/v), followed by crystallization from hexanes gave the product as fine white needles (2.10 g, 48%). $^1$H NMR (400 MHz, CDCl$_3$) δ: δ: 8.09 (d, J=8.8 Hz, 2H), 7.34 (d, J=8.8 Hz, 2H), 6.65 (d, J=17.2 Hz, 1H), 6.52 (s, 1H), 6.33 (dd, J$_1$=17.2 Hz, J$_2$=10.3 Hz, 1H), 6.08 (d, J=10.6 Hz, 1H), 2.61 (t, J=7.3 Hz, 2H), 1.74 (m, 2H), 1.36 (m, 4H), 0.91 (t, J=7.0 Hz, 3H) ppm. $^{13}$C (100 MHz, CDCl$_3$) δ: 1 96.3, 181.7, 163.6, 156.2, 133.9, 130.7, 128.9, 127.4, 122.5, 96.7, 38.2, 31.3, 25.8, 22.4, 13.9 ppm.

Example 7

The follow method serves as a general procedure for the synthesis of 1-(4-hydroxyphenyl)-3-phenyl-1,3-propanediones. The diketone (1-(4-hydroxyphenyl)-3-phenyl-1,3-propanedione) was prepared by heating 4-hydroxyacetophenone (10.00 g, 73.45 mmol), methyl benzoate (10.00 g, 73.45 mmol) and sodium hydride (7.05 g, 293 mmol) in methoxyethylether (diglyme) (200 mL) at 120° C. After heating the mixture for 3 hours, the solution was cooled to room temperature and quenched with isopropanol. The solvents were removed in vacuo and the residue was triturated with IM HCl (100 mL) and ethyl acetate (250 mL). The organic layer was successively washed with IM HCl (200 mL), deionized water (5×200 mL) and brine (1×100 mL). The organic layer was dried over sodium sulfate. Unreacted hydroxyacetophenone was removed by vacuum sublimation. The residue was adsorbed on silica and eluted from silica gel in toluene/ethyl acetate (9:1 v/v) to give the product as a mixture of isomers (yellow solid, 12.76 g, 72%). $^1$H NMR (400 MHz, Acetone-d$_6$) δ: (O—H not observed) 8.08 (m, 4H), 7.53 (m, 3H), 7.14 (s, 1H), 6.98 (m, 2H) ppm. $^{13}$C (100 MHz, Acetone-d$_6$) δ: 186.9, 183.6, 162.0, 135.5, 132.3, 130.0, 128.7, 127.1, 115.6, 92.0, ppm.

Examples 8–10

The following compounds were also prepared by appropriate modification of the method described in Example 7.

Example 8

Following the general procedure described in example 7, reaction of 4-hydroxyacetophenone (10.00 g, 73.45 mmol) with 4-(tert-butyl)methylbenzoate (14.12 g, 73.45 mmol) gave the product as a yellow crystalline solid (19.3 g, 88.9%).

Example 9

Following the general procedure outlined in example 7, reaction of 4-hydroxyacetophenone (7.60 g, 55.8 mmol) with 4-bromomethylbenzoate (12.00 g, 55.8 mmol) gave 18.02 g (98%) of the product as an impure oily brown solid. The product was purified by repeated elution from silica (toluene/ethyl acetate).

Example 10

Following the general procedure outlined in example 7, reaction of 4-hydroxyacetophenone (6.18 g, 45.4 mmol) with 4-(hexyl)methylbenzoate (10.00 g, 45.4 mmol) for 2 days gave as an impure low melting orange crystalline solid (14.26 g, 96.8%) which was purified by repeated elution from silica (toluene/ethyl acetate).

Example 11

The follow method serves as a general procedure for the synthesis of 1-(4-hydroxyphenyl)-3-phenyl-1,3-dioxaborines. A round bottom flask was charged with the title compound in example 7 (5.00 g, 20.8 mmol), boron-trifluoride acetic acid complex (3.91 g, 20.8 mmol) and dichloromethane. The mixture was heated at 50° C. for 12 hours, after which time the mixture was allowed to cool to room temperature. Filtration of the reaction mixture gave the product as a bright yellow crystalline solid that was crystallized from chloroform/hexanes (4.85 g, 83.5%). $^1$H NMR (400 MHz, Acetone-$d_6$) δ: 9.88 (s, 1H), 8.29 (m, 4H), 7.25 (m, 1H), 7.61 (m, 3H), 7.06 (m, 2H) ppm. $^{13}$C NMR (100 MHz, Acetone-$d_6$) δ: 182.7, 181.0, 164.9, 134.8, 132.5, 129.3, 128.7, 123.2, 116.5, 92.85 ppm.

Example 12

Following the general procedure outlined in example 11, the title compound from example 8 (1.00 g, 3.38 mmol) and BF$_3$(HOAc)$_2$ (0.63 g, 3.4 mmol) gave the product as a yellow microcrystalline solid (300 mg, 25.8%). $^1$H NMR (400 MHz, CDCl$_3$) δ: 9.85 (s, 1H), 8.30 (d, J=8.8 Hz, 2H), 8.24 (d, J=8.8 Hz, 2H), 7.68 (d, J=8.4 Hz, 2H), 7.61 (s, 1H), 7.08 (d, J=8.8 Hz, 2H), 1.36 (s, 9H) ppm. $^{13}$C NMR (100 MHz, Acetone-$d_6$) δ: 182.2, 181.1, 164.7, 159.0, 132.2, 129.8, 128.8, 126.2, 123.4, 116.4, 92.5, 35.5, 30.7 ppm.

Example 13

Following the general procedure outlined in example 11, the title compound from example 9, (17.5 g, 54.82 mmol) gave the product as a gold powder (12.97 g, 64.5%). $^1$H NMR (400 MHz, CDCl$_3$) δ: 9.96 (s, 1H), 8.31 (d, J=8.8 Hz, 2H), 8.22 (d, J=8.8 Hz, 2H), 7.82 (d, J=8.8 Hz, 2H), 7.67 (s, 1H), 7.07 (d, J=8.8 Hz, 2H) ppm. $^{13}$C NMR (100 MHz, Acetone-$d_6$) δ: 183.1, 179.6, 132.7, 132.5, 131.7, 130.4, 129.3, 123.1, 116.5, 93.0 ppm.

Example 14

Following the general procedure outlined in example 11, the title compound from example 10 (13.81 g, 42.57 mmol) and BF$_3$(HOAc)$_2$ (9.60 g, 51.1 mmol) gave the product as a yellow microcrystalline solid (10.89 g, 68.72%). $^1$H NMR (400 MHz, CDCl$_3$) δ: 8.03 (t, J=8.5 Hz, 4H), 7.34 (d, J=8.5 Hz, 2H), 7.04 (s, 1H), 6.96 (d, J=8.5 Hz, 2H), 6.06 (s, 1H), 2.69 (t, J=7.6 Hz, 2H), 1.64 (m, 2H), 1.30 (m, 6H), 0.88 (t, J=6.8 Hz, 3H) ppm. $^{13}$C NMR (100 MHz, CDCl$_3$) δ: 181.6, 162.5, 151.5, 131.8, 129.6, 129.3, 128.9, 124.3, 116.4, 92.2, 36.3, 31.7, 31.0, 29.0, 22.6, 14.1 ppm.

Example 15

The follow method serves as a general procedure for the synthesis of 1-(4-hydroxyphenyl)-3-phenyl-1,3-dioxaborine acrylates and methacrylates. A 3-neck flask was charged with the title compound in example 11 (4.73 g, 16.4 mmol) and THF (125 mL). The flask was fitted with a drying tube and two addition funnels. Separately, solutions of acryloyl chloride (2.96 g, 32.8 mmol) and triethylamine (7.0 g, 69 mmol) in THF (10 mL) were prepared. The reaction flask was cooled to 0° C. The solutions of triethylamine and acryloyl chloride were added dropwise over 30 minutes. The reaction mixture was then allowed to warm to room temperature overnight. Removal of the solvents in vacuo, followed by filtration through silica ($CH_2Cl_2$) and crystallization from toluene/hexanes gave the product as a microcrystalline yellow solid (4.36 g, 77.6%). $^1$H NMR (400 MHz, $CDCl_3$) δ: 8.21 (d, J=7 Hz, 2H), 8.15 (d, J=7 Hz, 2H), 7.7 (t, J=7 Hz, 1H), 7.56 (t, J=8.5 Hz, 2H), 7.36 (d, J=8.5 Hz, 2H), 7.17 (s, 1H), 6.68 (dd, $J_1$=17 Hz, $J_2$=1 Hz, 1H), 6.37 (dd, $J_1$=10 Hz, $J_2$=17 Hz, 1H), 6.10 (dd, $J_1$=10 Hz, $J_2$=1 Hz, 1H) ppm. $^{13}$C NMR (100 MHz, $CDCl_3$) δ: 183.5, 182.1, 163.6, 156.2, 135.4, 133.9, 132.0, 130.7, 129.5, 129.3, 129.0, 127.4, 122.5, 93.4 ppm.

Example 16

Following the general procedure outlined in example 15, reaction of the title compound from example 12 (5.65 g, 16.4 mmol) with acryloyl chloride (2.23 g, 24.6 mmol) gave the acrylate as a yellow powder (5.59 g, 85.4%). $^1$H NMR (400 MHz, $CDCl_3$) δ: 8.17 (d, J=9 Hz, 2H), 8.07 (d, J=9 Hz, 2H), 7.56 (d, J=8 Hz, 2H), 7.35 (d, J=8 Hz, 2H), 7.14 (s, 1H), 6.36 (dd, $J_1$=16 Hz, $J_2$=1 Hz, 1H), 6.33 (dd, $J_1$=11 Hz, $J_2$=17 Hz, 1H), 6.10 (dd, $J_1$=9 Hz, $J_2$=1 Hz, 1H), 1.34 (s, 9H) ppm. $^{13}$C NMR (100 MHz, $CDCl_3$) δ: 183.3, 181.4, 163.7, 160.1, 155.9, 133.8, 130.5, 129.5, 129.1, 127.4, 136.4, 122.493.1, 35.6, 31.0 ppm.

Example 17

Following the general procedure outlined in example 15, reaction of the title compound from example 13 (5.00 g, 13.6 mmol) with acryloyl chloride gave the product as a yellow powder (5.15 g, 89%).

Example 18

Following the general procedure outlined in example 15, reaction of the title compound from example 14 (7.85 g, 21.1 mmol) with acryloyl chloride gave the product as a yellow powder (8.42 g, 93%). $^1$H NMR (400 MHz, $CDCl_3$) δ: 8.14 (d, J=8.8 Hz, 2H), 8.03 (d, J=8.5 hz, 2H), 7.32 (d, J=8.5 hz, 4H), 7.10 (s, 1H), 6.62 (d, J=17 Hz, 1H), 6.31 (dd, $J_1$=10.4 Hz, $J_2$=17 Hz, 1H), 6.07 (d, J=10.4 Hz, 1H), 2.66 (t, J=8 Hz, 2H), 1.60 (m, 2H), 1.32 (br m, 6H), 0.84 (t, J=5.6 Hz) ppm.

Example 19

Following the general procedure outlined in example 15, reaction of the title compound from example 14 (2.68 g, 7.18 mmol) with methacryloyl chloride (0.825 g, 7.89 mmol) in the presence of triethylamine (0.800 g, 7.89 mmol) gave the product as a yellow powder (2.90 g, 91%). $^1$H NMR (400 MHz, $CDCl_3$) δ: 8.16 (d, J=8.8 Hz, 2H),8.05 (d, J=8.8 Hz, 2H), 7.33 (m, 4H), 7.14 (s, 1H), 6.39 (s, 1H), 5.83 (s, 1H), 2.70 (t, J=8 Hz, 2H), 2.07 (s, 3H), 1.64 (br m, 2H), 1.30 (m, 6H), 0.88 (t, 7 Hz, 3H) ppm. $^{13}$C (100 MHz, $CDCl_3$) δ: 183.3, 181.3, 165.0, 156.3, 152.1, 135.4, 130.5, 129.4, 129.2, 128.4, 122.5, 122.1, 93.0, 36.3, 31.7, 31.0, 29.0, 22.6, 18.4, 14.1 ppm.

Example 20

A Schlenk tube was charged with a stirbar, the title compound in example 5, AIBN, THF and DMF. The solution was degassed by bubbling a stream of dry argon through it for 15 minutes. The reaction mixture was heated to 70° C. overnight. The polymerization was quenched by pouring the reaction mixture into methanol (100 mL). The resulting slurry was stirred for 10 minutes, then filtered. The solid filtrate was collected, dissolved in CH$_2$Cl$_2$ (20 mL) and precipitated with methanol (200 mL). The filtrate was collected and dried overnight in the vacuum oven to give the product as a white powder.

Example 21

A Schlenk tube was charged with a stirbar, the title compound in example 6 (908 mg, 2.7 mmol), AIBN (4.4 mg, 0.03 mmol) and toluene (10.00 mL). The solution was degassed by bubbling a stream of dry argon through it for 15 minutes. The reaction mixture was heated to 70° C. overnight, at which time the product had separated from solution. The polymerization was quenched by pouring the reaction mixture into methanol (100 mL). The resulting slurry was stirred for 10 minutes then filtered. The solid filtrate was collected, dissolved in CH$_2$Cl$_2$ (10 mL) and reprecipitated with methanol (100 mL). The filtrate was collected and dried overnight in the vacuum oven to give the product as a white powder (weight average molecular weight (Mw)=112,000, polydispersity (PDI)=2.00, 445 mg, 49%). $^1$H NMR (400 MHz, CDCl$_3$) δ: 7.8 (br, 2H), 7.1 (br, 2H), 6.5 (br, 1H), 3.0 (br, 1H), 2.6 (br, 2H), 1.7 (br, 2H), 1.3 (br, 4H), 0.9 (br, 3H) ppm.

Example 22

A Schlenk tube was charged with a stirbar, the title compound in Example 15 (0.500 g, 1.4 mmol), ACHN (2.5 mg, 1.2 mmol) and toluene (10 mL). The resulting slurry was heated to 65° C. in an oil bath until all of the components had dissolved. The solution was then degassed by bubbling a stream of dry argon through it for 15 minutes. Once the mixture was degassed, the bath temperature was raised to 90° C. The reaction mixture was allowed to stir at 90° C. overnight. The polymerization was quenched by pouring the reaction mixture into methanol (100 mL). The resulting slurry was stirred for 10 minutes, and then filtered. The solid filtrate was collected, dissolved in CH$_2$Cl$_2$ (20 mL) and precipitated with methanol (200 mL). The filtrate was collected and dried overnight in the vacuum oven to give the product as yellow powder.

Examples 23–26

Polymers having the structures shown below were made by polymerization of the corresponding monomers in the manner described in example 22 above.

Example 23

Following the method used to generate the title compound in example 22, the title compound in example 16 yielded the desired polymer as a yellow powder.

Example 24

Following the method used to generate the title compound in example 22, the title compound in example 17 yielded the desired polymer as a yellow powder.

Example 25

Following the method used to generate the title compound in example 22, heating the title compound in example 18 (1.00 g, 2.18 mmol) with ACHN (5 mg) yielded the desired polymer as a yellow powder (Mw=29,000, PDI=2.7, 0.85 g, 85%). $^1$H NMR (400 MHz, CDCl$_3$) δ: 8.1–7.7 (br, 4H), 7.3–6.9 (br, 5H), 3.2–3.0, (br, 1H), 2.7–2.4 (br, 2H), 1.6–1.0 (br, 10H), 0.9–0.8 (br, 3H) ppm. $^{13}$C (100 MHz, CDCl$_3$) δ: 183, 180, 172, 170, 155, 152, 131, 130–128 (br), 122, 93, 36.3, 31.7, 30.9, 29.1, 22.6, 14.1 ppm.

Example 26

Following the method used to generate the title compound in example 22, the title compound in example 19 (0.500 g, 1.13 mmol) yielded the polymer as a yellow powder. (Mw= 110,000, PDI=1.42, 0.35 g, 70%). $^1$H NMR (400 MHz, CDCl$_3$) δ: 8.0 (br, 4H), 7.1 (br, 5H), 2.6 (br, 2H), 1.6–1.0 (br, 10H), 0.9 (br, 6H) ppm. $^{13}$C (100 MHz, CDCl$_3$) δ: 183, 180, 174, 155, 152, 130, 129–128 (br), 122.5, 122.0, 93, 46.3, 36.3, 31.6, 30.9, 29.0, 22.6, 14.1 ppm.

It will be appreciated by those skilled in the art that various omissions, additions and modifications may be made to the processes described above without departing from the scope of the invention, and all such modifications and changes are intended to fall within the scope of the invention, as defined by the appended claims.

What is claimed is:

1. A polydioxaborine having a weight average molecular weight of about 1,000 or greater.

2. The polydioxaborine of claim 1 comprising a dioxaborine group of the formula (I):

wherein $R_1$, $R_2$ $R_3$, $L_1$ and $L_2$ are each independently selected from the group consisting of hydrogen, linking atom, electron withdrawing group, and electron donating group.

3. The polydioxaborine of claim 2, wherein $L_1$ and $L_2$ are each independently selected from the group consisting of hydrogen, linking atom, halogen, $C_1$–$C_6$ alkyl, $C_1$–$C_6$ alkoxy, $C_1$–$C_6$ thioalkyl, nitrile, and a bridging ligand formed by $L_1$ and $L_2$ together;

wherein $R_1$ and $R_3$ are each independently selected from the group consisting of hydrogen, linking atom, carboxylate, carboxylic acid, aldehyde, amnide, epoxy, acid chloride, anhydride, nitrile, sulfonate, sulfonic acid, phosphonate, nitrate, nitro, $C_1$–$C_{18}$ alkoxy, $C_1$–$C_{18}$ alkyl, $C_1$–$C_{18}$ fluoroalkyl, hydroxyl, $C_{12}$–$C_{20}$ diarylamino, $C_2$–$C_{10}$ dialkylamino, $C_1$–$C_6$ alkylhalide, $C_1$–$C_6$ nitroalkyl, $C_1$–$C_6$ alkanoic acid, $C_1$–$C_6$ alkylamide, $C_6$–$C_{10}$ aryl, $C_6$–$C_{10}$ aryloxy, $C_7$–$C_{20}$ alkylaryl, and $C_7$–$C_{20}$ alkylaryloxy; and wherein $R_2$ is selected from the group consisting of hydrogen, linking atom, carboxylate, carboxylic acid, aldehyde, amide, epoxy, acid chloride, anhydride, nitrile, sulfonate, sulfonic acid, phosphonate, nitrate, nitro, $C_1$–$C_{18}$ alkoxy, $C_1$–$C_{18}$ alkyl, $C_1$–$C_{18}$ fluoroalkyl, $C_{12}$–$C_{20}$ diarylamino, $C_1$–$C_6$ alkylhalide, $C_1$–$C_6$ nitroalkyl, $C_1$–$C_6$ alkanoic acid, $C_1$–$C_6$ alkylamide, $C_7$–$C_{20}$ alkylaryl, and $C_7$–$C_{20}$ alkylaryloxy.

4. The polydioxaborine of claim 2, wherein the linking atom is selected from the group consisting of carbon atom, nitrogen atom, oxygen atom, and sulfur atom.

5. The polydioxaborine of claim 2, wherein $L_1$ and $L_2$ are each independently a halogen selected from the group consisting of fluoro, chloro, and bromo; $R_1$ is a linking atom, $R_2$ is hydrogen, and $R_3$ is selected from the group consisting of hydrogen, $C_1$–$C_{18}$ alkyl, $C_1$–$C_{18}$ alkoxy, $C_6$–$C_{10}$ aryl, $C_6$–$C_{10}$ aryloxy, $C_7$–$C_{20}$ alkylaryl, and $C_7$–$C_{20}$ alkylaryloxy.

6. The polydioxaborine of claim 2, wherein only one of $R_1$, $R_2$ $R_3$, $L_1$ and $L_2$ is a linking atom.

7. The polydioxaborine of claim 2, wherein two of $R_1$, $R_2$ $R_3$, $L_1$ and $L_2$ are linking atoms.

* * * * *

UNITED STATES PATENT AND TRADEMARK OFFICE
CERTIFICATE OF CORRECTION

PATENT NO. : 6,916,894 B2
APPLICATION NO. : 10/235182
DATED : July 12, 2005
INVENTOR(S) : J. Kevin Cammack, Seth R. Marder and Bernard Kippelen It is certified that error appears in the above-identified patent and that said Letters Patent is hereby corrected as shown below:

On Page 1, Column 1, Line 12, Delete "Soultions" and insert --Solutions--, therefor.
On Page 1, Column 2, Line 3, Delete "4idhyr" and insert --4idhydr--, therefore.
On Page 1, Column 2, Line 24, After "Matteson" delete ",".
On Page 1, Column 2, Line 24, Delete "Substitute" and insert --Substituted--, therefor.
On Page 1, Column 2, Line 34, Delete "[4,3b]" and insert --[4,3-b]--, therefor.
On Page 1, Column 2, Line 38, Delete "Schlemenz" and insert --Schiemenz--, therefor.
In Column 28, Line 54, In Claim 2, after "$R_2$" insert --,--.
In Column 28, Line 67, In Claim 3, delete "amnide" and insert --amide--, therefor.
In Column 30, Line 12, In Claim 6, after "$R_2$" insert --,--.
In Column 30, Line 14, In Claim 7, after "$R_2$" insert --,--.

Signed and Sealed this

Twelfth Day of December, 2006

JON W. DUDAS
*Director of the United States Patent and Trademark Office*